United States Patent [19]

Bryan et al.

[11] Patent Number: 4,657,959

[45] Date of Patent: Apr. 14, 1987

[54] HYDROPHILIC SILICONES

[75] Inventors: Thomas T. Bryan, Mahtomedi; Harvey L. Anderson, Dellwood, both of Minn.

[73] Assignee: Minnesota Mining and Manufacturing Company, St. Paul, Minn.

[21] Appl. No.: 798,737

[22] Filed: Nov. 15, 1985

[51] Int. Cl.$^4$ ................................................ C08K 5/24
[52] U.S. Cl. ..................... 524/266; 524/588; 524/730; 524/731; 524/858; 524/860; 264/16; 264/18; 264/19
[58] Field of Search ............... 524/266, 731, 730, 588, 524/858, 860; 264/16, 18, 19

[56] References Cited

U.S. PATENT DOCUMENTS

| | | | |
|---|---|---|---|
| re. 25,727 | 2/1965 | Haluska | 260/448.2 |
| 2,915,544 | 12/1959 | Holbrook | 260/448.2 |
| 3,057,901 | 10/1962 | Plueddemann | 260/448.2 |
| 3,398,104 | 8/1968 | Haluska | 260/2.5 |
| 3,402,192 | 9/1968 | Haluska | 260/448.2 |
| 3,505,377 | 4/1970 | Morehouse | 260/448.2 |
| 3,560,544 | 2/1971 | Haluska | 260/448.2 |
| 3,929,509 | 12/1975 | Taskler | 136/146 |
| 3,980,688 | 9/1976 | Litteral et al. | 260/448.2 |
| 4,100,124 | 7/1978 | Ichikawa et al. | 524/730 |
| 4,160,776 | 7/1979 | Scardera et al. | 260/448.2 |
| 4,226,794 | 10/1980 | Scardera et al. | 556/443 |
| 4,337,168 | 6/1982 | Scardera et al. | 252/312 |
| 4,354,873 | 10/1983 | Supcoe et al. | 106/18.32 |
| 4,395,454 | 7/1983 | Baldwin | 428/290 |
| 4,414,660 | 11/1983 | Wang et al. | 369/286 |
| 4,431,789 | 2/1984 | Okazaki et al. | 528/15 |
| 4,467,068 | 8/1984 | Maruyama et al. | 524/731 |
| 4,468,491 | 8/1984 | Steinberger et al. | 524/493 |
| 4,484,990 | 11/1984 | Bultman et al. | 204/106 |
| 4,510,227 | 4/1985 | Mohr et al. | 430/175 |
| 4,517,240 | 5/1985 | Tracton et al. | 428/326 |
| 4,537,944 | 8/1985 | Imai et al. | 524/731 |

OTHER PUBLICATIONS

Noll, W., "Chemistry and Technology of Silicones", 447–452 at 448 (1982).

Scott, G., Englebrecht, L., and Holdt, H. J., *Z. anorg. allg. Chem.*, 459, 177–186 (1979).

Vick, S. C., "Structure/Property Relationships for Silicone Polyalkyleneoxide Copolymers and Their Effect on Performance in Cosmetics", *Soap/Cosmetics/Chemical Specialties*, 60, (5), 36 (May 1984).

"Organomodified Oils [OMO]" (product literature from Union Carbide Corp., dated Apr. 1982).

"Silicate Cluster Fluids" (product literature from Olin Corp.).

"Silicones", *Kirk Othmer Encyclopedia of Chemical Technology*, 3rd Ed., 20, 922–962.

"Surfactants and Detersive Systems", *Kirk-Othmer Encyclopedia of Chemical Technology*, 3rd Ed., 22, 360–377 (1983).

"Silwet ® Surface Active Copolymers" (product literature from Union Carbide Corp., dated Oct. 1983).

"UCARSIL ® EPS Silicone Hydrophilic Finish" (product literature from Union Carbide Corp., dated Mar. 1984).

Lacy, A., Treleaven, S. and Jendresen, M. "The Effect of Selected Surfactants on the Wetting Behavior of Gypsum Die Stone on Impression Materials", *Cal. Dent. Assn. J.*, 5:36–40 (1977).

Norling, D. K. and Reisbick, M. H., "The Effect of Nonionic Surfactants on Bubble Entrapment in Elastomeric Impression Materials", *J. Pros. Dent.*, 42:342–347 (Sep. 1979).

*Primary Examiner*—Melvyn I. Marquis
*Attorney, Agent, or Firm*—Donald M. Sell; James A. Smith; David R. Cleveland

[57] ABSTRACT

Curable silicon prepolymers are made hydrophilic after cure by mixing the prepolymer with ethoxylated nonionic surface active agent or cationic or amphoteric fluorochemical surface active agent. The cured silicones have semipermanent hydrophilicity and are especially useful as dental impressions.

18 Claims, No Drawings

HYDROPHILIC SILICONES

TECHNICAL FIELD

This invention relates to curable silicone prepolymer compositions and cured silicone polymers. In another aspect, this invention relates to molded silicone articles. In a further aspect, this invention relates to dental impression materials.

BACKGROUND ART

Many different substances have been used as dental impression materials, each having its own advantages and disadvantages. An impression material must undergo a transformation, while in the mouth, from a viscous liquid to a rubbery solid. While factors such as taste, odor, toxicity, viscosity, cure speed, ease of demolding and strength after cure are all important, accuracy is of paramount concern. An impression material must accurately replicate the shape, size, and relative locations of both hard and soft tissues within the mouth. After cure, the impression must enable casting ("pouring") of an accurate model. The model usually is a plaster of Paris "stone" prepared from an aqueous gypsum slurry, which after setting represents a positive mold of the mouth. In recent years, silicones of both the condensation cure and addition cure varieties have become widely used as impression materials. They exhibit very good accuracy, together with an absence of taste and odor, easy demolding and other properties generally equivalent to or better than other commonly-used impression materials. However, silicone impression materials suffer from the disadvantage of hydrophobicity. This causes inaccurate impressions in moist fields, and discourages thorough wetting and accurate replication when the model is poured. In an attempt to provide better wetting of the impression by the gypsum slurry, some dental laboratories spray the cured impression with a detergent solution just prior to pouring the model.

Repeated attempts have been made to render silicones more hydrophilic by chemically modifying the siloxane backbone or by appending to the backbone various functional groups. Typical approaches are described in U.S. Pat. Nos. 4,259,467 (and in many of the references cited therein) and 4,332,922.

Siloxanes have been used as surface active agents, emulsifiers, defoamers or coatings, see, e.g. U.S. Pat. Nos. 3,057,901, 3,398,104, 3,402,192, 3,505,377, 3,560,544, 3,929,509, 3,980,688, 4,160,776, 4,226,794, 4,337,168, 4,395,454, 4,414,660, 4,431,789, 4,468,491, 4,510,227, 4,517,240 and Re. 25,727. Other publications describing the properties of siloxanes include "Silwet ® Surface Active Copolymers" (product literature from Union Carbide Corp., dated October, 1983), "Organomodified Oils [OMO]" (product literature from Union Carbide Corp., dated April, 1982), "UCAR-SIL ® EPS Silicone Hydrophilic Finish" (product literature from Union Carbide Corp., dated March, 1984), "Silicate Cluster ™ Fluids (product literature from Olin Corp.), and Vick, S.C., "Structure/Property Relationships for Silicone Polyalkyleneoxide Copolymers and Their Effects on Performance in Cosmetics", *Soap/Cosmetics/Chemical Specialties*, 60 (5), 36 (May, 1984).

U.S. Pat. No. 4,354,873 describes an antifouling coating for application to submerged boat hulls. The coating contains fumed silica, silicone oil, antifoulant, and an anionic, nonionic or amphoteric surfactant.

DISCLOSURE OF INVENTION

None of the above patents or publications disclose or suggest combination of a curable silicone prepolymer and a surfactant. The present invention provides, in one aspect, a curable silicone composition comprising a mixture of (a) curable silicone prepolymer and (b) surfactant selected from the group consisting of ethoxylated nonionic surface active agents and cationic or amphoteric fluorochemical surface active agents, said surfactant being present in sufficient amount and said ethoxylated nonionic surface active agent (if present) containing sufficient ethyleneoxy groups so that said composition, when cured, has a three minute water contact angle below about 65°. The cured composition is readily wet by water, yet retains the other desirable properties characteristic of silicones. The composition facilitates the making of more accurate dental impressions and the pouring of more accurate models.

The present invention also provides molded hydrophilic silicone articles prepared by shaping and curing such a composition. Such articles include dental impressions, lithographic plates, release liners, reflective sheeting, adhesives, coatings and sealants.

In addition, the present invention provides a method for making a dental impression, comprising the step of making a negative model of oral tissue using such a composition.

DETAILED DESCRIPTION

In the practice of the present invention, the curable silicone composition can be a one-part or multiple-part composition cured by the presence of adventitious moisture, crosslinking agents, catalysts, and/or heat. Most preferred are two-part addition cure or condensation cure compositions of the room temperature vulcanizing ("RTV") variety. The composition contains a "curable silicone prepolymer", that is, a polysiloxane having one or more functional groups which enable the prepolymer to be polymerized or cured to a state of higher molecular weight. Suitable silicone prepolymers are well-known in the art and are described, for example, in "Silicones", *Kirk-Othmer Encyclopedia of Chemical Technology*, 3rd Ed., 20, 922–962 (1982), the disclosure of which is incorporated herein by reference.

The surfactants used in the present invention are selected from ethoxylated nonionic surface active agents (for brevity, these will sometimes be referred to hereafter as "ethoxylated surfactants") and certain fluorochemical surface active agents (for brevity, these will sometimes be referred to hereafter as "fluorosurfactants"). Included among the surfactants useful in the present invention are ethoxylated nonionic surfactants containing perfluoroalkyl groups. These could be called ethoxylated surfactants or fluorosurfactants. They will be referred to herein as "ethoxylated surfactants", and the term "fluorosurfactants" will be used to refer to the remaining fluorochemical surfactants used in the present invention. Such fluorosurfactants are cationic or amphoteric fluorosurfactants.

The surfactant contains one or more solubilizing groups (e.g., one or more siloxane groups, hydrocarbyl groups or perfluoroalkyl groups) which render the surfactant soluble or dispersible in the silicone prepolymer. The surfactant also contains one or more water-loving groups which render a cured composition of the invention hydrophilic. When the surfactant is an ethoxylated surfactant, the water-loving groups are ethyleneoxy ($-C_2H_4O-$) groups or hydroxyalkyl-substituted ethyleneoxy (e.g., $-CH_2CH(CH_2OH)O-$) groups. For brevity, these water-loving groups will sometimes be collectively referred to hereafter as "ethyleneoxy" groups. When the surfactant is a fluorosurfactant, the water-loving groups are cationic groups or amphoteric groups, as described in more detail below.

The surfactant is present in a sufficient amount (and if it is an ethoxylated surfactant, it contains a sufficient number of ethyleneoxy groups) so that the silicone composition, when cured, has a three minute water contact angle below about 65°. The term "three minute water contact angle" refers to the contact angle formed by a drop of distilled water three minutes after it is applied to a cured composition of the invention, as measured at room temperature using a goniometer. Such contact angle measurements can be made as described in Noll. W., "Chemistry and Technology of Silicones", 447–452 at 448 (1982). Preferably, such measurements are conducted by curing a composition of the invention against a smooth substrate (e.g., a glass sheet), separating the substrate and silicone after cure, and placing the water drop on the smooth cured surface of the silicone. Preferably, the compositions of the invention have a three minute water contact angle below about 45°, more preferably below about 30°, and most preferably below about 10°.

The measured contact angle appears to be strongly dependent upon the amount of surfactant and, when the wetting agent is an ethoxylated surfactant, the number of ethyleneoxy groups present within the surfactant. In general, as the amount of surfactant increases, the water contact angle decreases. In general, as the number of ethyleneoxy groups in an ethoxylated surfactant increases beyond one, the water contact angle decreases to a minimum and then increases. The number of ethyleneoxy groups which provides the desired three minute water contact angle will vary depending upon several other factors, including the remaining substituent groups present in the ethoxylated surfactant. The effect of such other factors is illustrated in the examples set forth below. For example, the water contact angle tends to increase if propyleneoxy groups are present in the ethoxylated surfactant. Preferably no propyleneoxy groups are present in such surfactant.

It has also been found that the measured water contact angle increases if a cured composition is immersed in running water for a prolonged period of time. Without intending to be bound by theory, it is believed that the surfactant is dissolved or dispersed throughout the cured silicone compositions of the invention and can migrate therein and into adjacent fluids. When a drop of water is placed on a cured composition of the invention, it is believed that the surfactant migrates into the drop and reduces the interfacial surface tension between the water and the silicone. This hypothesis is supported by the above-noted increase in water contact angle after prolonged water exposure, and by two additional observations. First, the measured water contact angle slowly changes after the drop is placed on the surface of the cured silicone, generally reaching an equilibrium after about five minutes. Second, if the drop is observed using an optical comparator (which provides a highly magnified view of the drop), schlieren patterns become visible at the interface between the drop and the silicone within a few seconds after the drop is applied. As this takes place, the schlieren patterns diffuse throughout the drop and the drop slowly collapses and spreads out on the surface of the silicone.

In view of the above, the cured compositions of the invention perhaps are best regarded as having semipermanent hydrophilicity, that is, their hydrophilicity is subject to diminution upon prolonged contact with water. This dimunition is not a material drawback when making dental impressions, since the amount of water or other fluids which will come into contact with the impression is not excessive and in any event somewhat predictable in advance. A similar observation can be made in regard to other applications for the cured compositions of the invention (e.g., lithographic plates, release liners, reflective sheeting, adhesives, coatings and sealants). Additional applications for the compositions of the invention such as contact and intraocular lenses, silicone implants (e.g. artificial veins or mammary implants), and wound dressings may be possible, but would be contraindicated somewhat due to the longer-term fluid exposure involved and the possible adverse effects of surfactant migration.

Turning now to a more detailed discussion of the ethoxylated surfactant, the ethyleneoxy group(s) can be attached to the solubilizing group through either end of a ethyleneoxy group, that is, through a carbon atom or an oxygen atom of the ethyleneoxy group. Although the ethoxylated surfactant can contain as little as one ethyleneoxy group, preferably it contains at least three such groups, more preferably about five to fifteen such groups. The number of ethylenoxy groups should not be so large that the ethoxylated surfactant becomes waxy, as that may reduce its effectiveness. The ethoxylated surfactant also can contain other groups or substituents, if present in types and amounts which do not interfere with the functioning of such surfactant in the present invention or with the curing of the silicone prepolymer. Examples of such groups include propyleneoxy ($-C_3H_6O-$), vinyl, $-NH_2$, $-SH$ and oxirane groups.

The ethyleneoxy groups are preferably bonded to one another in series, and can be terminated with a hydrogen atom, an alkyl group, one or more propyleneoxy groups, or a solubilizing group of the type described above.

A preferred class of ethoxylated surfactants containing a siloxane solubilizing group has the average formula

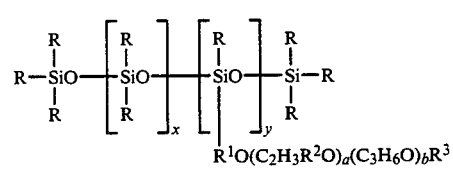

I where each R is independently a monovalent hydrocarbyl radical, $R^1$ is a divalent hydrocarbylene radical, each $R^2$ is independently hydrogen or a lower hydroxyalkyl radical, $R^3$ is hydrogen or a monovalent hydrocarbyl radical, x and b are independently greater than or equal to zero, and y and a are independently greater than or equal to one, with the proviso that a has a sufficient value and b is small enough so that a cured composition of the invention has the desired three minute water contact angle. Preferably in compounds of Formula I, R and $R^3$ are $-CH_3$, $R^1$ is $-C_3H_6-$, $R^2$ is hydrogen, x is zero or one, y is one to five, a is five to 20 and b is zero.

Another preferred class of ethoxylated surfactants has the average formula

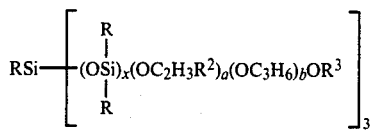

where R, $R^2$, $R^3$, x, a and b are as defined above. Preferably in compounds of Formula II, R and $R^3$ are —$CH_3$, $R^2$ is hydrogen, a is five to 20 and b is zero.

Ethoxylated surfactants of Formulas I and II above are described in the above-mentioned Union Carbide Corp. product literature and in U.S. Pat. Nos. 3,505,377, 3,980,688, and 4,431,789, the disclosures of which are incorporated herein by reference. Several of such ethoxylated surfactants are available from Union Carbide Corp. as "SILWET" surface active copolymers. Preferred SILWET surface active copolymers include SILWET L-77, L-7600 and L-7602. SILWET L-77 is an especially preferred ethoxylated surfactant. It is believed to have Formula I above, where R and $R^3$ are —$CH_3$, $R^1$ is —$C_3H_6$—, $R^2$ is hydrogen, x is zero or one, y is one or two, a is about seven and b is zero.

An additional preferred class of ethoxylated surfactants has the average formula

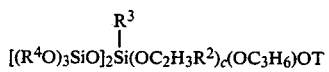

where $R^2$ and $R^3$ are as defined above, each $R^4$ group is independently a monovalent hydrocarbyl radical with the proviso that at least a majority of the $R^4$ groups are sterically hindered alkyl radicals having at least three carbon atoms, c is at least four, d is greater than or equal to zero, with the further proviso that c has a sufficient value and d is small enough so that a cured composition of the invention has the desired three minute water contact angle, and T is hydrogen, a monovalent alkyl or alkenyl radical, or a group of the formula —Si($R^3$)[OSi($OR^4$)$_3$]$_2$. Preferably in compounds of Formula III, $R^2$ is hydrogen, $R^3$ and T are —$CH_3$, $R^4$ is sec-butyl, c is five or more and d is zero. Representative ethoxylated surfactants of Formula III are described in the above-mentioned Olin Corp. product literature and in U.S. Pat. Nos. 4,160,776, 4,226,794, and 4,337,168, the disclosures of which are incorporated herein by reference. At least one such surfactant is experimentally available from Olin Corp. as a "SILFAC" polyethoxylated silicate cluster compound bearing the experimental designation "SILFAC 12M".

An additional preferred class of ethoxylated surfactants has the average formula $$(R^4O)_3Si(OC_2H_3R^2)_e(OC_3H_6)_fOT^1 \quad \text{IV}$$

where $R^2$ and $R^4$ are as defined above, e is at least four, f is greater than or equal to zero, with the further proviso that e has a sufficient value and f is small enough so that a cured composition of the invention has the desired three minute water contact angle, and $T^1$ is hydrogen, a monovalent alkyl or alkenyl radical, or a group of the formula —Si($OR^4$)$_3$. Such ethoxylated surfactants are believed to be novel and their preparation is described in more detail below. Preferably in compounds of Formula IV, $R^2$ is hydrogen, $R^4$ is sec-butyl, e is ten to 20, f is zero and $T^1$ is —Si(sec-butoxy)$_3$.

Suitable ethoxylated surfactants containing hydrocarbyl solubilizing groups are shown in "Surfactants and Detersive Systems", *Kirk-Othmer Encyclopedia of Chemical Technology*, 3rd Ed., 22, 360–377 (1983), the disclosure of which is incorporated herein by reference. A preferred class of such ethoxylated surfactants has the average formula

where $R^2$ is as defined above, $R^5$ is a saturated or unsaturated alkyl or alkylphenyl radical having at least seven carbon atoms, and g has a sufficient value so that a cured composition of the invention has the desired three minute water contact angle. Preferably in compounds of Formula V, $R^5$ is alkyl and g is at least about five.

Suitable ethoxylated surfactants containing perfluoroalkyl solubilizing groups are described in U.S. Pat. No. 2,915,544, the disclosure of which is incorporated herein by reference. A preferred class of such ethoxylated surfactants has the average formula

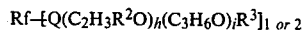

where $R^2$ and $R^3$ are as defined above, Rf is a fluorinated, monovalent or divalent, aliphatic, preferably saturated organic radical containing at least four carbon atoms and at least a terminal perfluoromethyl group, Q is a polyvalent (e.g., divalent) hydrocarbylene linking group (e.g., —$C_2H_4$—, or —$SO_2NR$— where R is as defined above), h is greater than or equal to one, and i is greater than or equal to zero, with the proviso that h has a sufficient value and i is small enough so that a cured composition of the invention has the desired three minute water contact angle.

The surfactant used in the present invention can also be a cationic or amphoteric fluorosurfactant. Such fluorosurfactants contain at least one perfluoroalkyl solubilizing group Rf where Rf is as defined above. The cationic fluorosurfactants contain at least one cationogenic group which is the radical of a base having an ionization constant in water at 25° C. of at least about $10^{-6}$. The amphoteric fluorosurfactants contain at least one such cationogenic group and at least one anionogenic group which is the radical of an acid having an ionization constant in water at 25° C. of at least about $10^{-6}$. Suitable fluorosurfactants are described, for example, in U.S. Pat. No. 4,484,990, the disclosure of which is incorporated herein by reference.

The compositions of the invention contain sufficient surfactant so that a cured composition of the invention has the desired three minute water contact angle. As pointed out above, when the amount of surfactant is increased, the three minute water contact angle generally decreases. As the amount of surfactant is increased further, the three minute contact angle reaches a minimum threshold value which does not decrease significantly with the use of additional surfactant. In general, a preferred amount of surfactant is an amount sufficient to provide a three minute water contact angle having such minimum threshold value. This preferred amount of surfactant also depends upon the particular curable silicone prepolymer chosen, the particular surfactant chosen, and the amounts and types of other adjuvants present in the compositions of the invention. Expressed on a weight basis, an effective amount of surfactant preferably is below about 30 weight percent, based on the total weight of the composition. More preferably, the amount of surfactant is about 0.25 to five weight percent, and most preferably about 0.5 to two weight percent.

The compositions of the invention are mixed, packaged and stored like conventional curable silicone compositions. In two-part compositions, the surfactant usually can be present in either part of the composition, or in both parts of the composition. However, where the surfactant may tend to react with either part of the composition (e g., if the surfactant contains one or more Si-H groups, and will be used in an addition cure polysiloxane), then the surfactant should be added only to a part of the composition with which it will not itself react. Mixtures of more than one surfactant can be used if desired.

The compositions of the invention can also contain adjuvants of the type customarily employed in curable silicone compositions. Such adjuvants include cross-linking agents, catalysts, fillers, pigments, reinforcing agents, plasticizers and the like.

The invention is illustrated in the following examples, in which all parts and percentages are by weight unless otherwise indicated. Because the examples are merely illustrative, they are not to be construed as limiting the scope of the invention.

EXAMPLE 1

Several surfactants were evaluated in a two-part vinylpolysiloxane impression material of the following formulation:

| Catalyst part: | |
|---|---|
| Vinyl-terminated polydimethylsiloxane, $M_n = 24,000$ | 46.3% |
| Silicone-treated silica[1] | 6.1 |
| Ground silica[2] | 46.9 |
| Catalyst made from a 2:1 mixture of 1,3-divinyl | 0.7 |

| -continued | |
|---|---|
| tetramethyl disiloxane and chloroplatinic acid | |
| Base part: | |
| Vinyl-terminated polydimethylsiloxane, $M_n = 24,000$ | 42.4% |
| Silicone-treated silica[1] | 7.3 |
| Ground silica[2] | 46.6 |
| Silicone crosslinking agent[3] | 3.7 |
| Tetravinyltetramethylcyclotetrasiloxane | 0.06 |

[1]"QUSO 545", Philadelphia Quartz.
[2]"IMSIL A-25", Illinois Minerals.
[3]A copolymer which on the basis of monomers charged would have an average composition $MD'_{10}D_{21}M$ where
$M = Si(CH_3)_3O_{0.5}$
$D = Si(CH_3)_2O$
$D' = Si(CH_3)HO$.

Each surfactant was added at a level of one percent (and in one instance two percent) to both parts of the above formulation. The two parts were then combined in equal proportions, mixed rapidly, poured into a cylindrical metal mold 19 mm in diameter × 1 mm in thickness sandwiched between two glass microscope slides, and allowed to cure for ten minutes at room temperature. A drop of distilled water was carefully placed on the cured surface and the contact angle formed by the drop was measured using a goniometer 30 seconds and three minutes after placement of the water drop. Set out below in TABLE I are the run number, surfactant, and measured water contact angles for each composition.

TABLE I

| | | Water contact angle | |
|---|---|---|---|
| Run no. | Surfactant | 30 sec. | 3 min. |
| 1 | None (control) | 100° | 99° |
| 2 | Polyalkylene oxide modified polymethylsiloxane ("Silwet L-77", Union Carbide Corp.) | 9° | 6° |
| 3 | Polyalkylene oxide modified polymethylsiloxane ("Silwet L-7600", Union Carbide Corp.) | 97° | 60° |
| 4 | Polyalkylene oxide modified polymethylsiloxane ("Silwet L-7602", Union Carbide Corp.) | 92° | 60° |
| 5 | $[(sec\text{-}butoxy)_3SiO]_2Si(CH_3)(OC_2H_4)_{12}OCH_3$ ("SILFAC 12M", Olin Corp.) | 36° | 22° |
| 6 | Polyethoxylated fatty alcohol ("Emulphor AM-310", GAF) | 33° | 28° |
| 7 | $(H_3C)_3CCH_2C(CH_3)_2C_6H_4(OC_2H_4)_{9-10}OH$ ("Triton X-100", Rohm & Haas) | 81° | 64° |
| 8 | $C_9H_{19}C_6H_4O(C_2H_4)_{9-10}OH$ ("Igepal CO-630", GAF) | 68° | 46° |
| 9 | Butoxypolypropyleneoxypolyethyleneoxyethanol ("Tergitol XD", Union Carbide Corp.)[1] | 55° | 50° |
| 10 | $C_8F_{17}SO_2N(C_2H_5)C_2H_4O(C_3H_6O)_8H$ | 60° | 55° |
| 11 | $C_8F_{17}SO_2N(C_2H_5)(C_2H_4O)_7H$ | 29° | 20° |
| 12 | $C_8F_{17}SO_2N(C_2H_5)(C_2H_4O)_{14}H$ | 78° | 26° |
| 13 | $C_8F_{17}SO_2NHC_3H_6N^+(CH_3)_3I^-$ | 102° | 40° |
| 14 | $C_6F_{13}SO_2N(CH_2CHOHCH_2SO_3^-)C_3H_6N^+(CH_3)_2C_2H_4OH^{(2)}$ | 72° | 64° |
| 15 | $C_8F_{17}SO_2N(C_2H_5)(CH_2)_2OCO(CH_2)_2NH(CH_2)_3Si(OCH_3)_3$ | 82° | 63° |

[1]Evaluated at two percent surfactant instead of at one percent. When evaluated at one percent, the 30 second water contact angle was 86° and the three minute water contact angle was 76°.
[2]Evaluated at one % solids, using a 25 percent solution in $C_4H_9OC_2H_4OC_2H_4OH$.

This example shows the useful improvement in water wettability obtained using the compositions of the invention. The composition of Run no. 2 was particularly effective. Slow cure (set) times were observed for the compositions of Run Nos. 9, 13 and 15.

COMPARATIVE EXAMPLE 1

One percent (and in one instance ten percent) additions of several comparison materials were evaluated in the impression material formulation of EXAMPLE 1. Set out below in TABLE II are the run number, comparison material, and measured water contact angles for each composition.

TABLE II

| | | Water contact angle | |
|---|---|---|---|
| Run no. | Comparison material | 30 sec. | 3 min. |
| 1 | Polyalkylene oxide modified polymethylsiloxane | 94° | 90° |

TABLE II-continued

| Run no. | Comparison material | Water contact angle 30 sec. | 3 min. |
|---|---|---|---|
| | ("Silwet L-720", Union Carbide Corp.) | | |
| 2 | Polyalkylene oxide modified polymethylsiloxane ("Silwet L-7002", Union Carbide Corp.) | 97° | 97° |
| 3 | $CH_3Si[OSi(sec\text{-}butoxy)_3]_3$ ("Silicate Cluster 102", Olin Corp.) | — | 105°[1] |
| 4 | $CH_3(OC_2H_4)_{7.2}OH$ | — | 76°[1] |
| 5 | $CH_3(OC_2H_4)_{7.2}OH$[2] | — | 76°[1] |
| 6 | Sodium lauryl sulfate ("Duponol ME", E.I. duPont de Nemours & Co.) | 91° | 88° |
| 7 | Organic phosphate ester, free acid ("Gafac PE-510", GAF Corp.) | 89° | 74° |
| 8 | Fatty amide ("Antaron FC-34", GAF Corp.) | 90° | 82° |
| 9 | 30:70 Copolymer of $C_8F_{17}SO_2N(CH_3)C_2H_4OCOC(CH_3)=CH_2$ and | 103° | 101° |
| 10 | $C_8F_{17}SO_3K$ | 89° | 88° |
| 11 | $C_7F_{15}COONH_4$ | 90° | 85° |

[1]Water contact angle measured at equilibrium. The three minute water contact angle would be the same or only slightly different.
[2]Evaluated at ten percent comparison material rather than one percent.

This example shows several comparison materials which did not provide the desired water contact angle. The materials of Run nos. 1 and 2 did not have a sufficient number of ethyleneoxy groups or had too many propyleneoxy groups. The materials of Run nos. 3, 6 through 8, 10 and 11 were not ethoxylated surfactants, cationic fluorosurfactants, or amphoteric fluorosurfactants. The material of Run nos. 4 and 5 did not have an appropriate solubilizing group. The material of Run no. 9 was a waxy solid.

EXAMPLE 2

A conventional two-part condensation cure silicone impression material ("Citricon" Dental Impression Resin, Kerr Division of Sybron Corp.) was made hydrophilic by the addition of one percent [(sec-butoxy)$_3$SiO]$_2$Si(CH$_3$)(OC$_2$H$_4$)$_{12}$OCH$_3$ to each part. The three minute water contact angle was reduced from 98° without surfactant to 28° with surfactant.

EXAMPLE 3

Varying amounts of [(sec-butoxy)$_3$SiO]$_2$Si(CH$_3$)(OC$_2$H$_4$)$_{12}$OCH$_3$ were added to both parts of the impression material formulation of EXAMPLE 1. The resulting compositions were cured and evaluated using the method of EXAMPLE 1, with water contact angles being measured at equilibrium rather than at three minutes. The water contact angles at three minutes typically would be the same or only slightly different. Set out below in TABLE III are the run number, percent surfactant, and equilibrium water contact angle for each composition.

TABLE III

| Run no. | % Surfactant | Equilibrium water contact angle |
|---|---|---|
| 1 | 0 | 100° |
| 2 | 0.125 | 102° |
| 3 | 0.25 | 48° |
| 4 | 0.5 | 34° |
| 5 | 1.0 | 32° |
| 6 | 2.0 | 27° |
| 7 | 15.0 | 26° |
| 8 | 30.0 | 21° |

This example illustrates the effect of variation in the amount of surfactant.

EXAMPLE 4

The composition of Run no. 6 of EXAMPLE 3 was cured in a two mm deep split mold made by stacking two of the one mm deep molds used in EXAMPLE 3. After curing the composition, the upper half of the mold was removed and the cured composition then sliced in half at the mold parting line using a razor blade. A water contact angle measurement was quickly performed on a sliced surface of the sample. At equilibrium, its water contact angle was 25°, compared to 27° tor Run no. 6 of EXAMPLE 3.

This example illustrates that the interior of a cured composition of the invention is hydrophilic.

EXAMPLE 5

Varying amounts of the ethoxylated surfactant "Silwet L-77" were added to both parts of the impression material formulation of EXAMPLE 1. The resulting compositions were cured and evaluated using the method of EXAMPLE 1. Set out below in TABLE IV are the run number, percent surfactant, and three minute water contact angle for each composition.

TABLE IV

| Run no. | % Surfactant | 3 Minute water contact angle |
|---|---|---|
| 1 | 0 | 100° |
| 2 | 0.25 | 67° |
| 3 | 0.50 | 45° |
| 4 | 0.75 | 12° |
| 5 | 1.00 | 9° |

This example also illustrates the effect of variation in the amount of surfactant.

EXAMPLE 6

A series of silicate "cluster" surfactants having the following average formula were synthesized using the method shown in Example 1 of U.S. Pat. No. 4,226,794:

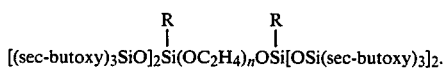

One percent of each of these surfactants was added to both parts of the impression material formulation of EXAMPLE 1. Set out below in TABLE V are the run number, identity of R and n, and the equilibrium water contact angle for each composition.

TABLE V

| Run no. | R | n | Equilibrium water contact angle |
|---|---|---|---|
| 1 | H— | 13.2 | 52° |
| 2 | CH$_3$— | 3.0 | 92° |
| 3 | CH$_3$— | 8.7 | 65° |
| 4 | CH$_3$— | 13.2 | 56° |

TABLE V-continued

| Run no. | R | n | Equilibrium water contact angle |
|---|---|---|---|
| 5 | CH$_2$=CH— | 13.2 | 66° |
| 6 | CH$_2$=CH— | 34.6 | 59° |

An additional series of silicate "cluster" surfactants of the following average formula was synthesized using the method shown in Example 2 of U.S. Pat. No. 4,160,776:

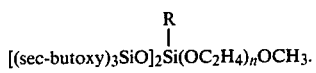

$$[(\text{sec-butoxy})_3\text{SiO}]_2\text{Si}(\text{OC}_2\text{H}_4)_n\text{OCH}_3.$$

One percent of each of these surfactants was added to both parts of the impression material formulation of EXAMPLE 1. Set out below in TABLE VI are the run number, identity of R and n, and the equilibrium water contact angle for each composition.

TABLE VI

| Run no. | R | n | Equilibrium water contact angle |
|---|---|---|---|
| 1 | H— | 7.2 | 39° |
| 2 | CH$_3$— | 7.2 | 31° |
| 3 | CH$_3$— | 11.8 | 32° |
| 4 | CH$_3$— | 16.3 | 37° |
| 5 | CH$_2$=CH— | 2.0 | 88° |
| 6 | CH$_2$=CH— | 7.2 | 49° |
| 7 | CH$_2$=CH— | 11.8 | 28° |
| 8 | CH$_2$=CH— | 42.5 | 100° |

This example shows the effect variations in structure have upon the hydrophilicity of a cured composition of the invention.

EXAMPLE 7

Tri(sec-butoxy)chlorosilane was prepared according to the procedure described in Schott, G., Englebrecht, L., and Holdt, H. J., *Z. anorg. allg. Chem.*, 459, 177–186 (1979). A 56.5 g portion of the resulting product was added dropwise to a stirred solution of 60 g of a polyethyleneglycol having the average formula HO(C$_2$H$_4$O)$_{13.2}$H ("Carbowax 600", Union Carbide Corp.) and 16 g pyridine in 300 ml toluene. The resulting mixture was heated to 70° C. for two hours, then allowed to cool to room temperature and filtered to remove pyridine hydrochloride. Toluene was removed from the mixture using a rotary evaporator. Final traces of toluene and unreacted pyridine were removed under high vacuum (10$^{-2}$ Torr). The product was a clear, colorless to faint yellow fluid. NMR and IR analyses were consistent with the average structure (sec-butoxy)$_3$SiO(C$_2$H$_4$O)$_{13.2}$Si(sec-butoxy)$_3$. Using $^1$H NMR analysis with CDCl$_3$ as solvent, delta values were 0.90(18H,d,—CHCH$_3$), 1.17 (18H,t,—CH$_2$CH$_3$), 1.45 (12H,q,—CH$_2$CH$_3$), 3.61 (53H,s,OCH$_2$CH$_2$), and 3.87 (6H,—CH). Using IR analysis, absorption peaks occurred at 2898, 1485, 1379, 1351, 1330, 1299, 1258, 1117, 1058, 1018, 960, 862, 816 and 735 cm$^{-1}$.

When one percent of this novel ethoxylated surfactant was added to both parts of the impression material formulation of EXAMPLE 1, the cured composition had 30 second and three minute water contact angles of 44° and 32°, respectively.

EXAMPLE 8

Using the method of EXAMPLE 7, and substituting a variety of alkoxylated linear alcohols or diols for the polyethyleneglycol used in EXAMPLE 7, a series of novel alkoxylated surfactants having the average formula (R$^4$O)$_3$Si(OC$_2$H$_4$)$_e$(OC$_3$H$_6$)$_f$OT$^1$ were synthesized. Using the method of EXAMPLE 1, one percent of each of these surfactants was added to both parts of the impression material formulation of EXAMPLE 1. Set out below in TABLE VII are the run number, identity of R$^4$, e, f and T$^1$, and the equilibrium water contact angle for each composition.

TABLE VII

| Run no. | R$^4$ | e | f | T$^1$ | Equilibrium water contact angle |
|---|---|---|---|---|---|
| 1 | sec-butyl | 2 | 0 | —CH$_3$ | 90° |
| 2 | sec-butyl | 7.2 | 0 | —CH$_3$ | 56° |
| 3 | sec-butyl | 11.8 | 0 | —CH$_3$ | 72° |
| 4 | sec-butyl | 16.3 | 0 | —CH$_3$ | 84° |
| 5 | sec-butyl | 42.5 | 0 | —CH$_3$ | 98° |
| 6 | sec-butyl | 3 | 0 | T'$^{(1)}$ | 76° |
| 7 | sec-butyl | 6.4 | 0 | T' | 63° |
| 8 | sec-butyl | 8.7 | 0 | T' | 57° |
| 9 | sec-butyl | 13.2 | 0 | T' | 36° |
| 10 | sec-butyl | 22.3 | 0 | T' | 59° |
| 11 | sec-butyl | 0 | 16.9 | T' | 71° |
| 12 | sec-butyl | 0 | 18.8 | T' | 66° |
| 13 | sec-butyl | 0 | 34.2 | T' | 73° |
| 14 | sec-butyl | 0 | 51.4 | T' | 76° |
| 15 | (2) | 7.2 | 0 | —CH$_3$ | 44° |
| 16 | (2) | 16.3 | 0 | —CH$_3$ | 59° |
| 17 | (2) | 13.2 | 0 | T''$^{(3)}$ | 85° |
| 18 | (2) | 22.3 | 0 | T'' | 76° |

$^{(1)}$T' = —Si(sec-butoxy)$_3$.
$^{(2)}$Two sec-butoxy groups and one allyloxy group were attached to the Si atom shown in the formula.
$^{(3)}$T'' = —Si(sec-butoxy)$_2$(allyloxy).

This example shows several novel surfactants, and the effect variation in their structure has upon the hydrophilicity of a cured composition of the invention.

EXAMPLE 9

Three curable silicone compositions were formulated as in EXAMPLE 1, using one percent [(sec-butoxy)$_2$SiO]$_2$Si(CH$_3$)(OC$_2$H$_4$)$_{12}$OCH$_3$ in the catalyst portion, base portion or both portions of the formulation. The cure time of each composition was measured at 24° C. (using a "Monsanto" oscillating disk rheometer) immediately after preparing the compositions, and after aging the compositions for seven days at 60° C. The results are set out below in TABLE VIII.

TABLE VIII

| Surfactant added to | | Cure time, minutes:seconds | |
|---|---|---|---|
| Catalyst | Base | Unaged | Aged 7 days @ 60° C. |
| No | No | 5:15$^{(1)}$ | 4:45$^{(1)}$ |
| Yes | No | 5:00 | 4:55 |
| No | Yes | 4:34 | 4:30 |
| Yes | Yes | 4:55 | 4:50 |

$^{(1)}$Average of several runs.

Comparable results were obtained when this example was repeated using the ethoxylated surfactant "Silwet L-77".

This example demonstrates the excellent storage stability which can be obtained with these compositions.

EXAMPLE 10

The composition of Run no. 5 of EXAMPLE 1 was prepared without silica fillers. The equilibrium water contact angle of the cured composition was 28°, compared to 32° when fillers were included.

This example illustrates that the use of filler did not materially affect hydrophilicity.

EXAMPLE 11

The composition of Run no. 1 of EXAMPLE 5 was cured and washed in cold running tap water for two days. The measured water contact angle (as observed using an optical comparator) increased from 20°–23° before washing to 60°–63° after washing. Schlieren patterns could be observed within the water drop when it was placed on the cured silicone surface. This example indicates that the surfactant may have migrated from the silicone into the wash water and into the water drop.

EXAMPLE 12

The composition of Run no 1 of EXAMPLE 5 was extruded in a thin stream into a tray of water. The extrudate tended to maintain its shape underwater. A composition prepared without surfactant tended to "ball-up" underwater, perhaps in order to minimize its exposed surface area. This example indicates that the compositions of the invention may yield impressions with improved accuracy in submerged fields, such as impressions of the gingival sulcus made in the presence of crevicular fluids.

EXAMPLE 13

The composition ot Run no. 4 of EXAMPLE 5 was used to make an impression ot a qrooved aluminum block according to the procedure of American Dental Association Specification No. 19. The composition produced an excellent impression which passed the specification. It also passed if the aluminum block was flooded with water before taking the impression. A composition prepared without surfactant passed if the aluminum block was dry but failed if the block was wet.

EXAMPLE 14

Several silicone impression material formulations and comparison polyether impression material formulations were cast in a rectangular prismatic mold to form a cast bar 57 mm long×20 mm wide×four mm thick. The mold had been previously scribed with two marks across its long dimension, spaced 50 mm apart. These marks were reproduced in the cast bar. Each bar stored at room temperature and 32 percent or 100 percent relative humidity for 24 hours, then removed and measured to determine if the spacing between the scribed marks had changed. Set out below in TABLE IX are the run number, impression material, and the measured dimensional change at each relative humidity.

TABLE IX

| Run no. | Impression material | Dimensional change | |
|---|---|---|---|
| | | 32% R.H. | 100% R.H. |
| 1 | Control[1] | +0.02% | +0.21% |
| 2 | Control +0.75% "Silwet L-77"[2] | −0.07% | +0.22% |
| 3 | Polyether[3] | +0.08% | +0.64% |

TABLE IX-continued

| Run no. | Impression material | Dimensional change | |
|---|---|---|---|
| | | 32% R.H. | 100% R.H. |
| 4 | Polyether[4] | −0.04% | +0.75% |

[1]A composition like that of Run no. 1 of EXAMPLE 1 but containing in the catalyst part 42.4% vinyl-terminated polydimethylsiloxane, 4.4% silicone-treated silica, 50.6% ground silica, 0.6% catalyst, and 2.1% pigment, and containing in the base part 37.8% vinyl terminated polydimethyldisiloxane, 4.4% silicone-treated silica, 52.4% ground silica, 2.7% silicone crosslinker of average composition $MD'_{6.8}D_{10}M$, 0.7% silicone crosslinker of average composition $MD'_{10}D_{21}M$, 2% pigment, and 0.03% tetravinyltetramethylcyclotetrasiloxane. Average of two samples.
[2]Average of three samples.
[3]"Impregum Impression Material Type 1", Premier Dental Products.
[4]"Polyjel", L. D. Caulk Company.

This example illustrates the excellent dimensional stability of compositions of the invention even when stored under conditions of high humidity.

EXAMPLE 15

A two-part impression material formulation was prepared from the following ingredients:

| Catalyst part: | |
|---|---|
| Vinyl-terminated polydimethylsiloxane, $M_n$ = 70,000 | 15.0% |
| Vinyl-terminated polydimethylsiloxane, $M_n$ = 24,000 | 6.4 |
| Silicone-treated silica | 2.7 |
| Ground silica | 33.0 |
| Calcium carbonate[1] | 35.7 |
| Catalyst | 0.15 |
| Ethoxylated surfactant[2] | 0.5 |
| White mineral oil, USP | 6.5 |
| Base part | |
| Vinyl-terminated polydimethylsiloxane, $M_n$ = 70,000 | 12.1% |
| Vinyl-terminated polydimethylsiloxane, $M_n$ = 24,000 | 5.2 |
| Silicone-treated silica | 2.7 |
| Ground silica | 33.7 |
| Calcium carbonate[1] | 36.4 |
| Silicone crosslinker[3] | 2.0 |
| Pigment | 0.6 |
| Ethoxylated surfactant[2] | 0.75 |

[1]"Vicron", Pfizer Corp.
[2]"Silwet L-77".
[3]Copolymer of average composition $MD'_{6.8}D_{10}M$.

This composition was used to make impressions of the oral tissue of ten patients. Most patients could detect a slight taste, but none found it objectionable. Those patients that noticed a taste judged it to be much better than the taste of rubber-base or polyether impression materials. An additional impression was made of the oral tissue of a patient who had previously experienced a severe allergic reaction to a commercial polyether impression material. She detected no taste and did not experience any allergic reaction of other adverse symptoms.

EXAMPLE 16

A two-part impression material formulation was prepared from the following ingredients:

| Catalyst part: | |
|---|---|
| Vinyl-terminated polydimethyldixiloxane, Mn = 24,000 | 41.4% |
| Silicone-treated silica | 4.3 |
| Ground silica | 52.7 |
| Ethoxylated surfactant[1] | 0.75 |
| Catalyst | 3.0 |
| Pigment | 0.5 |
| Base part: | |
| Vinyl-terminated polydimethylsiloxane, Mn = 24,000 | 30.0% |
| Silicone-treated silica | 4.4 |
| Ground silica | 54.1 |
| Silicone crosslinker[2] | 7.3 |

-continued

| Pigment | 0.35 |
| Ethoxylated surfactant[1] | 0.75 |

[1]"Silwet L-77".
[2]Copolymer of average composition $MD'_{6.8}D_{10}M$.

This composition was used to make impressions of the oral tissue of three pateints. Excellent detail reproduction was obtained.

EXAMPLE 17

A typical full crown preparation was made on the upper left lateral incisor of a "Typodont" dental model. Two custom impression trays were prepared by lining the trays with the hydrophilic impression material of EXAMPLE 15 or with a corresponding non-hydrophilic impression material prepared without ethoxylated surfactant. Two final impressions were taken by lining these custom trays with the hydrophilic impression material of Run No. 5 of EXAMPLE 1 or with the non-hydrophilic impression material of Run No. 1 of EXAMPLE 1, respectively. Models of the cured impressions were poured using "Vel-Mix Stone" (Kerr Division of Sybron Corp.). The model made from the hydrophilic impression materials was evaluated by three consulting dentists, and regarded by each as superior to the model made from the non-hydrophilic impression materials, especially in detail reproduction.

Comparable results were obtained when this example was repeated by taking impressions of the oral tissue of several human patients. The observed superiority of the models made from the hydrophilic impression materials was especially apparent for impressions made under moist field conditions.

Various modifications and alterations of this invention will be apparent to those skilled in the art without departing from the scope and spirit of this invention and the latter should not be restricted to that set forth herein for illustrative purposes.

We claim:

1. A curable silicone composition comprising a mixture of (a) curable silicone prepolymer and (b) surfactant selected from the group consisting of (i) ethoxylated nonionic surface active agents containing one or more siloxane or perfluoroalkyl solubilizing groups and (ii) cationic or amphoteric fluorochemical surface active agents, said surfactant being present in sufficient amount and said ethoxylated nonionic surface active agent, if present, containing sufficient ethyleneoxy groups so that said composition, when cured, has a three minute water contact angle below about 65°.

2. A composition according to claim 1, wherein said curable silicone prepolymer comprises a two-part RTV addition cure or condensation cure polysiloxane.

3. A composition according to claim 1, wherein said surfactant comprises said ethoxylated nonionic surface active agent.

4. A composition according to claim 3, wherein said agent contains at least three unsubstituted or hydroxyalkyl-substituted ethyleneoxy groups.

5. A composition according to claim 4, wherein said agent contains about five to fifteen unsubstituted ethyleneoxy groups.

6. A composition according to claim 3, comprising surfactant having the following average formulas I or II:

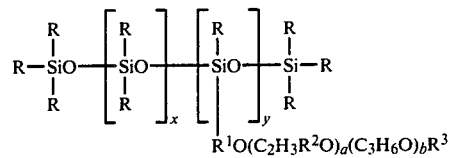

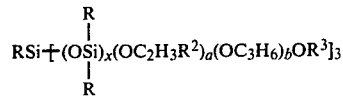

wherein each R is independently a monovalent hydrocarbyl radical, $R^1$ is a divalent hydrocarbylene radical, each $R^2$ is independently hydrogen or a lower hydroxyalkyl radical, $R^3$ is hydrogen or a monovalent hydrocarbyl radical, x and b are independently greater than or equal to zero, and y and a are independently greater than or equal to one, with the proviso that a has a sufficient value and b is small enough so that said composition, when cured, has a three minute water contact angle below about 65°.

7. A composition according to claim 6, wherein R and $R^3$ are $-CH_3$, $R^1$ is $-C_3H_6-$, $R^2$ is hydrogen, x is zero or one, y is one to five, a is five to 20 and b is zero.

8. A composition according to claim 7, wherein said curable silicone prepolymer comprises a two part RTV addition cure polysiloxane, said surfactant has said formula I, y is one or two, a is about seven, and said contact angle is below about 30°.

9. A composition according to claim 3, wherein said surfactant has the average formula

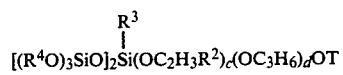

wherein each $R^2$ is independently hydrogen or a lower hydroxyalkyl radical, $R^3$ is hydrogen or a monovalent hydrocarbyl radical, each $R^4$ group is independently a monovalent hydrocarbyl radical with the proviso that at least a majority of the $R^4$ groups are sterically hindered alkyl radicals having at least three carbon atoms, c is at least 4, d is greater than or equal to zero with the further proviso that c has a sufficient value and d is small enough so that said composition, when cured, has a three minute water contact angle below about 65°, and T is a monovalent alkyl or alkenyl radical or a group of the formula $-Si(R^2)[OSi(OR^4)_3]_2$.

10. A composition according to claim 9, wherein curable silicone prepolymer comprises a two part RTV addition cure polysiloxane, $R^2$ is hydrogen, $R^3$ and T are $-CH_3$, $R^4$ is sec-butyl, c is 5 or more, d is zero, and said contact angle is below about 45°.

11. A composition according to claim 3, wherein said surfactant has the average formula

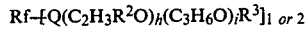

wherein Rf is a fluorinated, monovalent or divalent, aliphatic organic radical containing at least four carbon atoms and at least a terminal perfluoromethyl group, Q is a polyvalent hydrocarbylene linking group, each $R^2$ is independently hydrogen or a lower hydroxyalkyl radical, $R^3$ is hydrogen or a monovalent hydrocarbyl radical, h is greater than or equal to one, and i is greater than or equal to zero, with the proviso that h has a sufficient value and i is small enough so that said composition, when cured, has a three minute water contact angle below about 65°.

12. A composition according to claim 1, wherein said surfactant comprises said fluorochemical surface active agent.

13. A cured silicone composition, comprising polysiloxane polymer having dissolved or dispersed therein surfactant selected from the group consisting of (a) ethoxylated nonionic surface active agents containing one or more siloxane or perfluoroalkyl solubilizing groups and (b) cationic or amphoteric fluorochemical surface active agents, said surfactant being present in sufficient amount and said ethoxylated nonionic surface active agent, if present, containing sufficient ethyleneoxy groups so that said composition has a three minute water contact angle below about 65°, said composition having semipermanent hydrophilicity.

14. A composition according to claim 13, in the form of a dental impression comprising a negative mold of oral tissue.

15. A composition according to claim 14, wherein said impression has a three minute water contact angle below about 45°.

16. A composition according to claim 13, in the form of a lithographic plate, release liner, reflective sheet, adhesive, coating or sealant.

17. A method for making a dental impression, comprising the step of making a negative mold or orgal tissue using as said mold a curable silicone composition comprising a mixture of (a) RTV addition cure or condensation cure polysiloxane prepolymer and (b) surfactant selected from the group consisting of (i) ethoxylated nonionic surface active agents containing one or more siloxane or perfluoroalkyl solubilizing groups and (ii) cationic or amphoteric fluorochemical surface active agents, said surfactant being present in sufficient amount and said ethoxylated nonionic surface active agent, if present, containing sufficient ethyleneoxy groups so that said composition, when cured, has a three minute water contact angle below about 65°.

18. A method according to claim 17, wherein said surfactant has the average formula

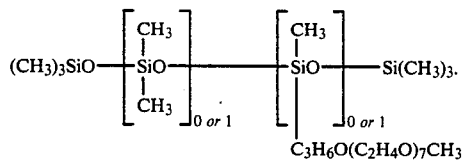

* * * * *